Jan. 8, 1963 C. FISCHER Plant Pat. 2,215
GLADIOLUS PLANT
Filed March 27, 1962
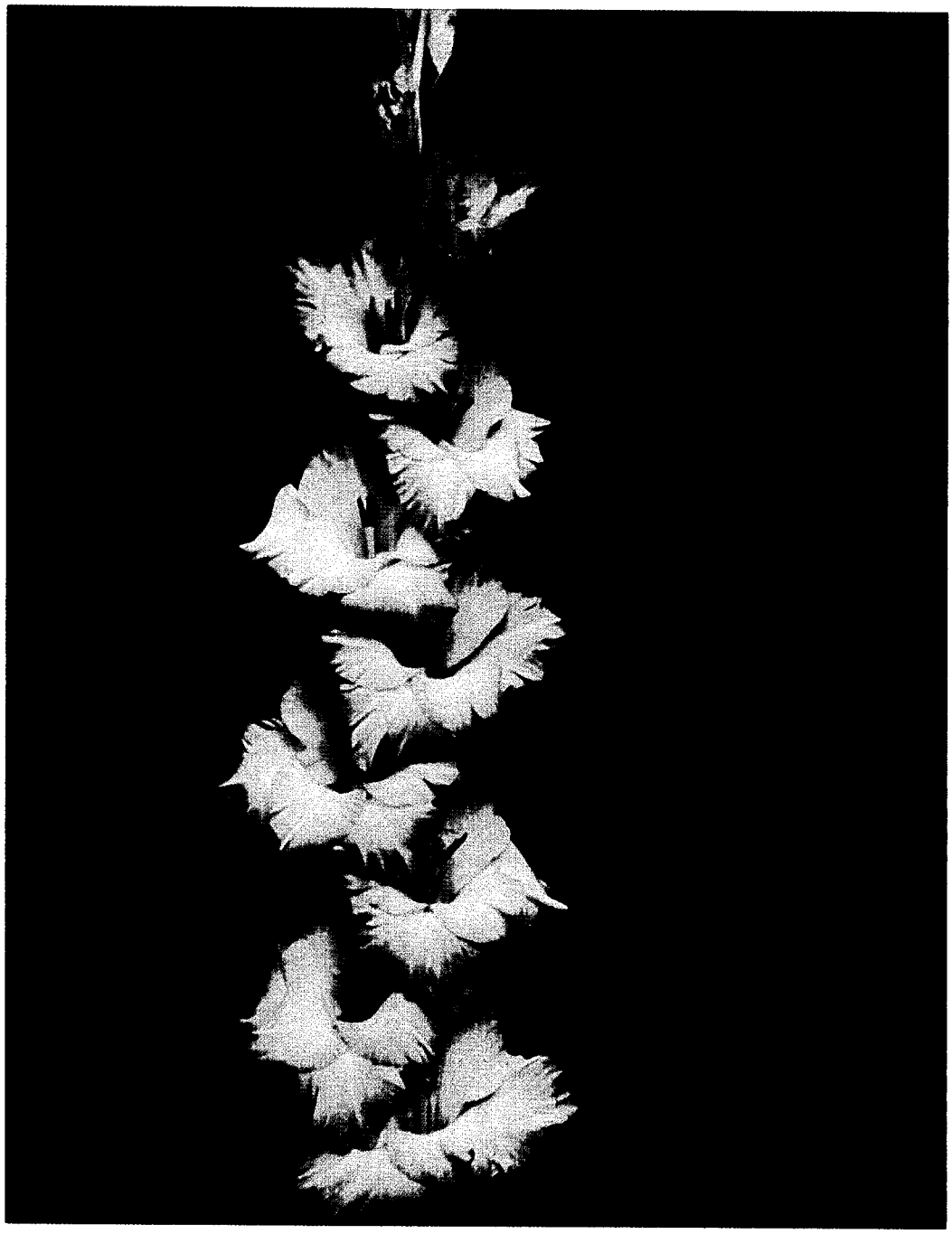
Inventor.
Carl Fischer
By: Robb & Robb
Attorneys.

United States Patent Office

Plant Pat. 2,215
Patented Jan. 8, 1963

2,215
GLADIOLUS PLANT

Carl Fischer, St. Charles, Minn., assignor to Imperial Flowers Limited, Leamington, Ontario, Canada, a corporation of Canada Filed Mar. 27, 1962, Ser. No. 182,984
1 Claim. (Cl. 47—60)

The present invention relates to a new and distinct variety of gladiolus plant which was originated by me by crossing the variety "Better Times" (unpatented) with an unnamed and unpatented seedling derived from a cross of "Rose O'Day" (unpatented) × "Elizabeth the Queen" (unpatented), the variety "Better Times" being the seed parent and the unnamed seedling being the pollen parent.

As the result of this breeding, I have produced a new gladiolus variety which is characterized by the following unique combination of characteristics which are outstanding therein and which distinguish it from its parents, as well as from all other varieties of which I am aware:

(1) A rugged and vigorous habit of growth;
(2) A prolific blooming habit;
(3) Long, tapering flower heads; and
(4) A distinctive and attractive general color tonality of the flowers which are a clear and bright blue color and which have a smooth white throat.

My new variety resembles its parent "Better Times" more than any other known variety, but differs therefrom principally by being more rugged in its habit of growth, being more prolific in its blooming habit, having longer flower heads, and the flowers having a clear white throat, while "Better Times" has a darker colored throat.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagtions from cormels.

*Plant*

Growth: Vigorous; blossom spike attains height averaging about 54 inches to 60 inches; extremely prolific.

Blooming habit: An early to mid-season bloomer in the northern latitudes of the United States; comes into bloom from the planting of large bulbs in about 75 to 80 days.

Stems: Slender and willowy. Diameter at base—½ inch.

Foliage: Upright; attains height of about 32 inches; leaves range from 1½ inches to 1¾ inches wide. Color—green.

Disease resistance: Unusually resistant to Fusarium yellows, Sclerotinia dry rot and Septoria leaf spot, as determined by comparison with other varieties grown in my fields near St. Charles, Minnesota, in irrigated black loam soil.

Corms (bulbs): High-crowned; with thin papery husks showing a rose cast where the husk is attached to the bulb. Color of flesh—creamy white.

*Flower*

Spike: Tall; willowy; bears from 21 to 23 buds, with 3 or 4 buds opening the first day, and thereafter with 7 or 8 opening at one time.

Bud:
- *Size.*—From 3 inches to 3½ inches long when opening; smaller in size at the tip.
- *Opening.*—5 or 6 buds show color at one time.

Flower:
- *Arrangement.*—Florets are semi-formally arranged on the stem and all face forward.
- *Size.*—Individual florets average about 4¾ inches in diameter; upper blooms progressively smaller.
- *Form.*—Florets are round, ruffled, and recurved, with slightly raised midribs.

Petals:
- *Shape.*—Broad; round; recurved; with raised midribs on the inner petals.
- *Size.*—Upper petals—2 inches wide. Lip petal—1½ inches wide.
- *Aspect.*—Average substance.
- *Fragrance.*—None.
- *Color.*—Blending from Veronica Violet, Plate 639/1 at edges to Veronica Violet, Plate 639/3 at lightest part, with white throat and faint white midribs; throat of opening buds is Naples Yellow, Plate 403/2, fading to White in open floret.

*Reproductive Organs*

Stamens: Color—Veronica Violet, Plate 639 at bottom, with white at top.

Pistil: Color—white.

I claim:

A new and distinct variety of gladiolus plant, substantially as herein shown and described, characterized particularly as to novelty by the unique combination of a rugged and vigorous habit of growth, a prolific blooming habit, long and tapering flower heads, and a distinctive and attractive clear bright blue general color tonality of the flowers, said flowers having a smooth white throat.

No references cited.